(12) United States Patent
Schiefer

(10) Patent No.: US 7,222,517 B2
(45) Date of Patent: May 29, 2007

(54) METHOD FOR DETERMINING THE CHARACTERISTIC PROPERTIES OF SOOT PARTICLES

(75) Inventor: Erich Schiefer, Graz (AT)

(73) Assignee: AVL List GmbH, Graz (AT)

( * ) Notice: Subject to any disclaimer, the term of this patent is extended or adjusted under 35 U.S.C. 154(b) by 96 days.

(21) Appl. No.: 10/860,647

(22) Filed: Jun. 4, 2004

(65) Prior Publication Data
US 2004/0244582 A1 Dec. 9, 2004

(30) Foreign Application Priority Data
Jun. 4, 2003 (AT) .............................. GM387/2003

(51) Int. Cl.
*G01N 37/00* (2006.01)
(52) U.S. Cl. .................. 73/28.01; 73/28.03; 73/31.07; 73/863.21; 73/863.22; 95/19
(58) Field of Classification Search .... 73/28.01–28.06, 73/31.07, 863.21–863.25
See application file for complete search history.

(56) References Cited

U.S. PATENT DOCUMENTS

| | | | | |
|---|---|---|---|---|
| 4,406,155 A | * | 9/1983 | Krachler et al. | ........... 73/23.33 |
| 4,788,819 A | * | 12/1988 | Henkel | ........................ 60/303 |
| 5,882,379 A | * | 3/1999 | Johnson | ........................ 95/19 |
| 5,996,422 A | * | 12/1999 | Buck et al. | .............. 73/863.03 |
| 6,016,688 A | * | 1/2000 | Hiss et al. | .................. 73/28.01 |
| 6,056,792 A | * | 5/2000 | Barr et al. | ..................... 44/403 |
| 6,136,067 A | * | 10/2000 | Dehn et al. | ..................... 95/20 |
| 6,391,102 B1 | * | 5/2002 | Bodden et al. | .............. 96/417 |
| 6,423,118 B1 | * | 7/2002 | Becerra et al. | ................ 95/19 |
| 6,691,509 B2 | * | 2/2004 | Hoffman et al. | ............. 60/286 |
| 6,911,062 B1 | * | 6/2005 | Taylor | ....................... 55/385.1 |
| 6,969,413 B2 | * | 11/2005 | Yahata et al. | .............. 55/282.3 |
| 7,041,157 B1 | * | 5/2006 | Fleck | ........................... 95/273 |
| 2004/0244582 A1 | * | 12/2004 | Schiefer | ........................ 95/19 |
| 2005/0091970 A1 | * | 5/2005 | Nieuwstadt | .................. 60/297 |
| 2006/0144124 A1 | * | 7/2006 | Kusaka et al. | ............. 73/23.33 |
| 2006/0169136 A1 | * | 8/2006 | Avery et al. | .................... 95/19 |

* cited by examiner

Primary Examiner—Hezron Williams
Assistant Examiner—Samir M. Shah
(74) Attorney, Agent, or Firm—Dykema Gossett PLLC

(57) ABSTRACT

A method for determining the characteristic properties of soot particles originating from combustion processes utilizes the determination of the blackening of a filter paper. In order to allow for achieving a quick and relatively accurate determination of the particle sizes, possibly of further characteristics as well, a method of this kind provides that the pressure conditions on the filter paper are established as well. It is advantageous for this purpose to determine the differential pressure on the filter and/or filter paper caused by the deposition of the particles.

22 Claims, 4 Drawing Sheets

METHOD FOR DETERMINING THE CHARACTERISTIC PROPERTIES OF SOOT PARTICLES

BACKGROUND OF THE INVENTION

1. Field of the Invention

The invention relates to a method for determining the characteristic properties of soot particles from combustion processes by way of determining the blackening of a filter paper.

2. The Prior Art

Smoke meters of the current generation establish the filter smoke number (FSN) or the soot emission in mg/m$^3$ by means of the deposition of particles on a filter paper. Due to the possibility of varying the suction length and suction time, it is possible to vary the measuring range in the context of such a method within very wide limits. The measured values range approximately from FSN 0.001 to 10, which corresponds to measured concentration values of approximately 0.015 to 30000 mg/m$^3$.

But measuring the size of the emitted particles is, on the one hand, either quite time-consuming or quite complex and, on the other hand, in part very expensive equipment is necessary for the process. Examples of equipment of this kind include impactors, however, they have the disadvantage of long measuring times and the requirement of having to weigh the collected particles; electrical low pressure impactors (ELPI), a low-pressure impactor type with dynamic measurement; and particle mobility analyzers such as scanning mobility particle sizers (SMPS) or double differential mobility particle sizers (DDMPS), etc.

Currently, the composition of the particles can only be established either by way of chemical extraction—with diverse solvents, such as dichloromethane—or by way of thermogravimetric methods, which means by way of sample heating. To this end, the particles must be collected in a defined filter, weighed and submitted for analysis according to one of the methods referred to above—including weighing of the filters following the filter treatment.

The object of the present invention therefore consists in providing a method that allows for the simple, quick and relatively accurate determination of the particle sizes and possibly of further characteristics as well.

SUMMARY OF THE INVENTION

In order to achieve this object, the method is characterized by the fact that, additionally, the pressure ratios on the filter paper are established. Surprisingly, it was found that by way of determining the pressure drop on the filter paper and the value of the paper blackening PS and/or the specific filter loading FB (given as weight per cross sectional surface of the filter used, in mg/m$^2$), or based on the functional correlation of these values, it is possible to establish the mean particle diameter. It is also possible to roughly characterize the particles (solid or liquid) or, assuming a certain distribution function, it is possible to ascertain a rough approximate value for the number of particles.

For this purpose, it is advantageous to determine the differential pressure that is produced on the filter or the filter paper due to the deposition of the particles.

An advantageous embodied example of the invention envisions the integral determination of the differential pressure.

But, in the alternative, it is also possible to establish the differential pressure by way of resolution per time unit.

To be able to hold the length of the measurement for a wide range of particle concentrations within certain limits, it is advantageous to envision that the face velocity of the filter surface is in the range of 1 to 200 cm/sec, preferably in the range of 5 to 50 cm/sec. Specifically for very small concentrations, such as emissions of 50 µg/m$^3$ soot or less, higher face velocities may be necessary in order to arrive at a measured value within times comprising several seconds to several minutes. Reducing the face velocity in high concentrations to the lower limit may result in better selectivity.

In a first embodiment of the invention, the absolute pressure before and after the filter is established.

On the other hand, it can also be envisioned that the pressure is determined before and after the filter relative to the ambient air pressure, or the differential pressure is determined across the filter and the absolute pressure of the ambient air.

To be able to take all parameters of the gas flow correctly into account for the measurement, it is envisioned according to a further characteristic of the invention that the temperature in the proximity of the filter surface be ascertained.

It is advantageous to carry out this process in such a way that the filter temperature and/or the inside temperature of the measuring device is/are maintained constant.

In this context, the filter is preferably maintained at a constant temperature within the range of 50 to 190° C., preferably between 60 and 70° C.

A further preferred embodiment of the invention provides that the temperature of the particle-loaded measured gas is regulated in such a way that it has the same temperature as the filter and/or the inside temperature of the measuring device.

In correspondence with another advantageous embodiment of the method according to the invention, the change of the suction length relative to the suction length during measurement of particle-laden gas is determined relative to the suction length determined with clean papers in ultra-pure air, with corresponding values always being placed in relation to the same framework conditions.

Advantageously, the method according to the invention envisions that the measurement is conducted on the filter paper at least with one preset differential pressure value.

These preset differential pressure threshold values are in a range of 0 to 300 mbar, preferably in a range of 25 to 200 mbar, in preferred embodied examples.

Alternatively to providing a preset value of a certain differential pressure, it is also possible to envision that the measurement be done with at least one preset negative pressure value (meaning pressure value lower than ambient pressure) after the filter.

In this case, these predefined negative pressure threshold values are in the range of 50 to 450 mbar, preferably in the range of 50 to 300 mbar.

In accordance with another preferred embodiment of the invention, the measurements are conducted with at least two different suction lengths.

It is also possible to envision the measuring process to involve at least two varying differential pressures and/or negative pressures.

Advantageously, it is also possible to realize a method variation which provides that the change of the differential pressure on the filter paper and/or the negative pressure after the filter paper are/is established by way of the specific filter loading length, and the value of the specific filter loading is determined at the end of the loading of the filter.

The invention will be described in further detail in the following description with respect to preferred embodiments. Explanatory diagrams are provided for the figures shown in the drawings.

DETAILED DESCRIPTION OF THE PREFERRED EMBODIMENTS

Figure 1:
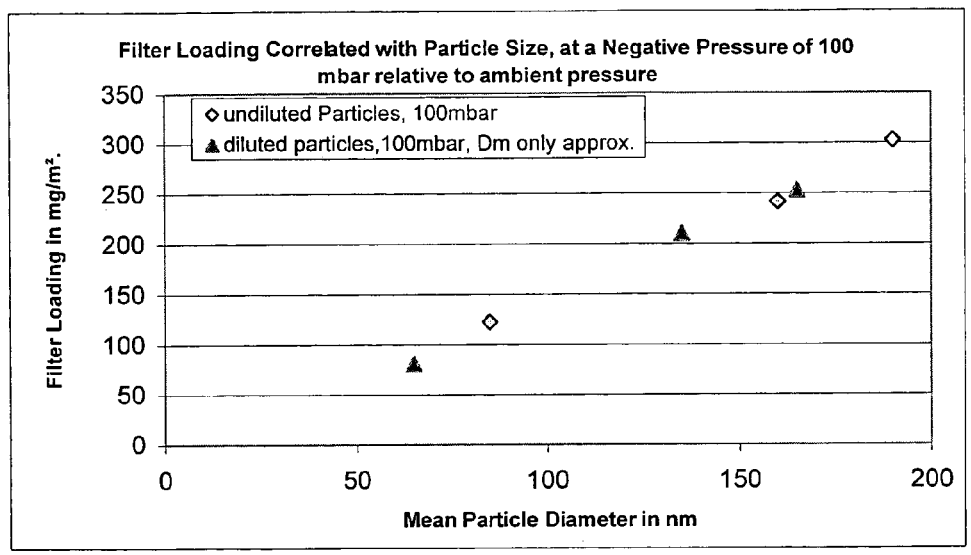
FIG. 1 shows the correlation between specific filter loading and the mean particle size.

FIG. 1 shows, for a firm preset negative pressure threshold of 100 mbar after the filter paper and relative to a preset starting value, the connection between particle diameter (in nm) and specific filter loading (in mg/m$^2$). Measurements of diluted and undiluted particles: The term undiluted particle refers to the particles in the form and concentration occurring, for example, during the combustion process in the engine; while mixing with pure air or a pure inert gas can, if necessary, result in a dilution of the concentration, a state referred to as "diluted particles." The consequence of a dilution is usually that the mean particle diameters, which are extracted for the purpose of the measurement at a preset sampling location, are smaller than as if undiluted, a circumstance that is also illustrated in the diagram in FIG. 1. The dilution in fact reduces the agglomeration of the primary particles with diameters of typically approximately 10 to 20 nm that occurs during the combustion process; this agglomeration process takes place otherwise on the way of the particles to the sampling location and then to the measuring cell.

The measurements are carried out fully automatically in this instance—starting with a certain starting pressure that is caused by the gas flow itself—until a low pressure of 100 mbar is reached due to the deposition of the particles on the filter paper, and afterwards the degree of blackening of the filter paper (=paper blackening) is measured; consequently, based on the total suction volume or suction length, the specific filter loading with "soot" is calculated in mg/m$^2$.

The measured values were obtained with a CAST particle generator. The carbon part of the particles was larger, approximately 70% of the total particles (measured by way of extraction with dichloromethane) and >85% in accordance with the thermogravimetric method. The particle diameters (undiluted) originate from SMPS (scanning mobility particle sizer) data, the diluted values were extrapolated on the basis of similar comparative diluted/undiluted measurements (with DDMPS).

Figure 2:
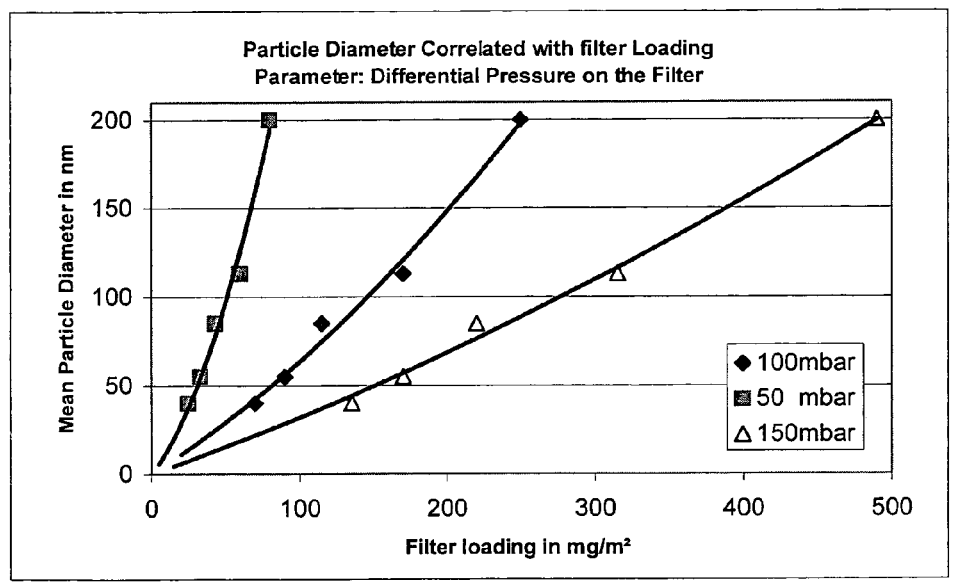
FIG. 2 is a diagram showing the correlation of the particle diameter and the measured specific filter loading at different pressures.

FIG. 2 depicts the equivalent relation for different differential pressure thresholds on the filter paper. The points are comprised of points which are calculated by way of interpolation from real measured data at different pressure drops on filter papers. The data are measured using a smoke meter 4155. The represented parameter "differential pressure" is the pressure drop across the filter paper that is caused by the deposited particles.

Depending on the face velocity, a certain portion of the pressure drop on the filter paper is caused, on the one hand, by the flow resistance of the filter paper and, on the other hand, by the deposited particles. With increasing face velocity the pressure drop (square effect) becomes higher while, additionally, more particle mass is deposited, resulting in the ability to obtain a correspondingly big signal quickly. The pressure drop that is measured overall is defined by the constant pressure drop on the filter by the measured gas itself, the quantity and the packing density of the particles deposited thereon, the density of the measured gas and the face velocity. With constant loading, the differential pressure is also constant here.

The curves and correlations in FIGS. 1 and 2 are indicated for single-mode particle size distributions (typical log normal distributions) and a soot/solid substance part of larger than approximately 30% to 100%.

But the fact that these relations can also be achieved via other measured values of the smoke meter is demonstrated in various examples and evaluation methods as explained in the following.

The connection between paper blackening (PS) and specific filter loading (FB) is expressed by way of the following relation:

$$\text{Specific filter loading FB}\,[\text{mg/m}^2] = \quad (1)$$
$$PS*5.32*\text{EXP}(0.3062*PS) \text{ for } PS \text{ smaller } 8 = PS*2.015*$$
$$\text{EXP}(0.4264*PS)*(1+7.8*((PS-8)/2)\wedge 10) \text{ for } PS \text{ larger } 8$$
$$PS = 10 \text{ for complete blackening of the paper (reflectivity}=0\%);$$
$$PS = 0 \text{ for white, non-blackened paper (refectivity}=100\%).$$

Figure 3:
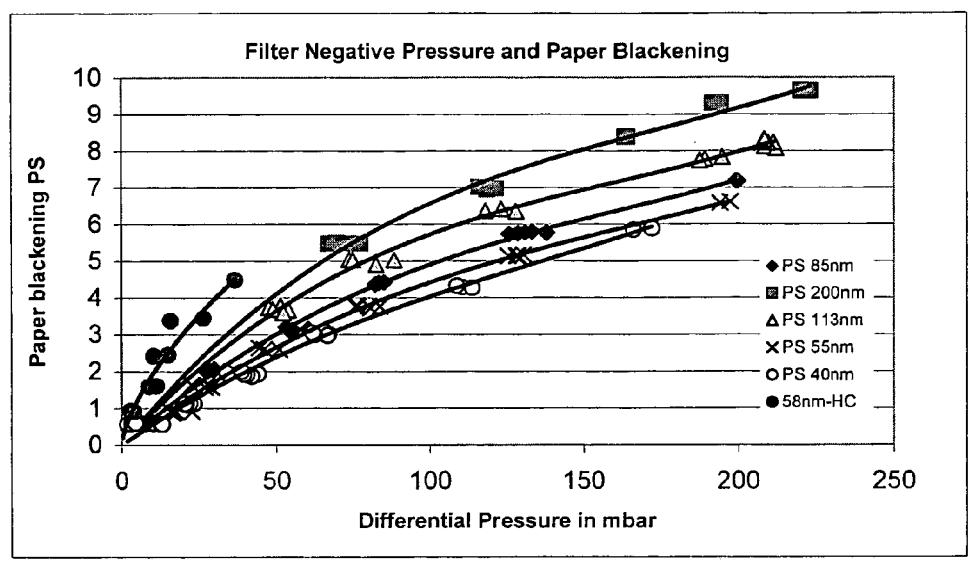
FIG. 3 demonstrates the correlation between the negative pressure on the filter and the measured paper blackening for different particle sizes.

These functions shown in the diagram in FIG. 3 indicate the correlation between pressure change and paper blackening PS and therefore FB; in this context, particle size and the particle type (HC) are indicated as parameters.

Figure 4:
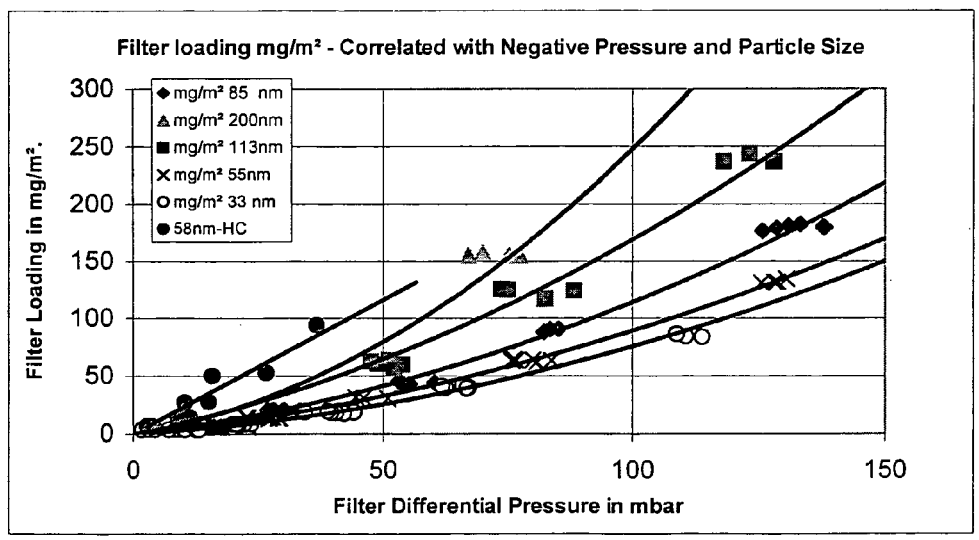
FIG. 4 corresponds to the diagram in FIG. 3 with regard to the correlations associated with the specific filter loading FB in mg/m$^3$.

The diagram in FIG. 4 corresponds to the diagram in FIG. 3, but now the correlations for the specific filter loading FB in mg/m$^2$ are indicated. The crossing points 50, 100 and 150 mbar produce the correlations that are shown in FIGS. 1 and 2.

Also represented in FIGS. 3 and 4 is the correlation for particles of 58 nm mean size which are comprised of tar-like hydrocarbons (HC) at more than 90%. Even though these particles, that are dominated by HC, are not characterized by the curves in images 1 and 2, the functional relation between the change of the low pressure and the filter loading applies for these particles based on a strict Lambert-Beer adsorption law correlation, which means that these particles can also be unambiguously assigned by way of consulting the measured data—measured at different negative pressures—or analysis of the time-specific pressure change in conjunction with the filter loading for the purpose of the examination.

It is therefore possible to characterize particles with a more complex composition by way of an analysis of the composition of the line function.

The inaccuracy of the measured values that is seemingly shown in FIGS. 3 and 4 is only feigned by an inaccuracy of the measured values of the differential pressure occurring during the measurements.

Figure 5:
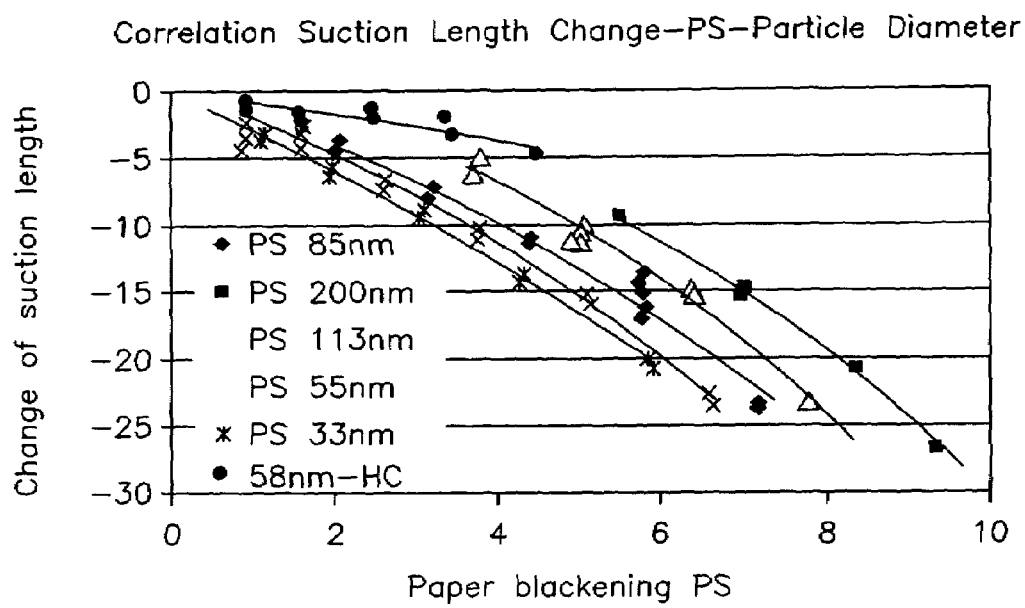
FIG. 5 shows the correlation between the change of suction length and particle diameter.

Referring to FIG. 5, a further possibility for analysis of the correlations is represented. In this context, the change of the suction length during measurements with particles is viewed as a function of the paper blackening PS. The change of the suction length is represented in %, relative to the suction length on the same filter paper, but in ultra-pure air and with the same time length used to measure the particles.

The suction length is, in this instance, the length of the gas column in m, cm or mm that is pulled across the filter paper during the measurement.

Algorithm: LR(t) reference suction length at suction time/length of measurement time t without particle loading LM (t): Measured suction length with suction time t during particle measurement PS: Measured paper blackening (PS 10=100% reflectivity loss, =0% reflectivity)

$$\text{Change of } SL := 100*(LM(t)-LR(t))/LR(t) \quad (2)$$

Based on this type of representation, in the same way as for the diagrams in FIGS. 1 and 2, it is possible to arrive at a similar but not completely identical correlation. As in FIGS. 3 and 4, FIG. 5 also demonstrates that the correlation for the HC particles also takes a clearly different course here than that for solid-substance-like soot particles which are dominated by the carbon part.

As an alternative to the suction length, it is also possible to use the suction volume (or even the duration of the suction time) as parameter, translating into the following correlation between suction length and suction volume:

$$\text{Suction volume}=\text{suction length}*\text{cross-sectional surface of the filter paper} \quad (3)$$

Correspondingly, the determinative cross-sectional surface of the filter paper is the surface through which the particles are aspirated and on which the particles are deposited causing the paper blackening in PS.

Using this effect that solid-substance particles exhibit a functionally different behavior between negative pressure and paper blackening and/or the suction length change behavior across the duration of the suction time than "soft" liquid or quasi-liquid particles, such as drops of condensate or particles dominated by the HC part, it is possible to additionally determine—at least roughly—by means of a defined test algorithm as to whether the measured particles exhibit the characteristics of a solid substance or of a liquid.

It is possible to distinguish in this way as to whether the measured particles are primarily comprised of generally condensed HC's, such as fuel/oil/HC-condensate, or carbon.

To be noted as a further parameter for the existence of primarily "liquid" particles is the fact that the absorption behavior or the paper blackening as a function of the suction volume satisfies a different functional correlation than with particles that are primarily dominated by solid carbon, which allows characterizing the particles also based on this behavior.

The optical behavior when "liquid" absorbing particles dominate, that are deposited on the filter papers, satisfies across wide areas up to a paper blackening of PS>5 a correlation according to the Lambert-Beer law between paper blackening PS, suction length L and concentration of the particles in the measured gas.

$$(100-PS*10)=100*EXP(-k*L)$$

$$\text{or}(100-PS*10)=100*EXP(-Konz*Qext*L) \quad (4)$$

with the extinction coefficient k in m−1 being proportional to the concentration (Konz.) in $g/m^3$, Qext=extinction cross-section of the particles (material constant) in $m^2/g$, L is the suction length in m. The relation between concentration and specific filter loading FB is indicated with:

$$\text{Concentration [in } g/m^3\text{] is proportional FB [in } g/m^2\text{]/suction length [in m]} \quad (5)$$

The correlation resulting for the HC particles in accordance with equation 4 is not identical with the formalism of equations 1 and 5 for solid-substance-like soot particles which means that, based on these deviations for different suction times, it is possible to distinguish between the particle types.

A deviating correlation presents itself (—described with the formalism in equation 1—) for solid-substance-like particles, such as carbon, due to the structured deposition of the particles on the filter surface resulting in a granulation-like optical light/dark structure on the filter surface, thereby causing deviations from the correlation according to Beer-Lambert of the light absorption (and light reflection).

But for the same reasons it is principally possible to determine the particle size and also the particle composition on the basis of these measured data as well, i.e., when measuring the paper blackening at different suction volumes, the calculation of the functional relationship between PS and suction length and the deviations relative to the correlation according to Lambert-Beer and/or the deviations relative to the formalism according to equation 1.

Figure 6:
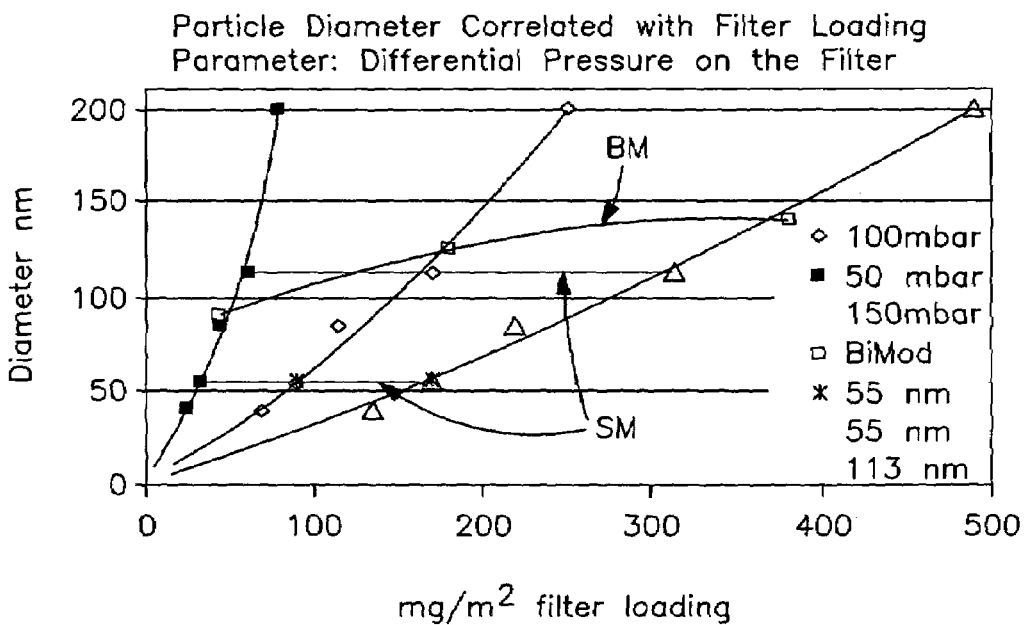
FIG. 6 shows the loading of the filter surfaces at different differential pressures on the filter paper.

In individual cases it is also possible to encounter bimodal particle distributions in the context of the emission measurements of particles. FIG. 6 shows how even such complex distribution functions can be assigned still correctly at least for solid-substance-like soot particles by utilizing this method.

Lines SM in FIG. 6 show the correlations for single-mode particles with log normal distribution of the particle sizes around a mean particle diameter (=diameter nm in the graphic). It is always the same diameter that results for single-mode particles for the different low pressures, irrespective of the differential pressure on the filter. Line BM shows the determined particle diameter at different differential pressures for a bimodal particle distribution. A clear deviation can be observed from the lines SM with a particle diameter of 80 nm resulting at 50 mbar and a diameter of 145 nm at 150 mbar. (The particles are composed approximately at a ratio of 1:1 of particles with mean diameters of approximately 60 nm and approximately 220 nm). This means at small negative pressures the differential pressure at the filter is dominated by the small particulate fraction, while at large pressures the mean value of both factions dominates (60+ 145 nm=205).

Moreover, by way of using different kinds of filter papers—exhibiting different efficiencies in terms of particle collection—it is furthermore possible to adapt the range for the determination of the particle diameters to include other soot sources that emit soot particles with essentially larger and also essentially smaller diameters.

The measured values in the embodiments of the invention that are explained in the diagrams in FIGS. 1 to 6 were measured with a filter paper that has a filter particle collection efficiency of 50% for DOP normal particles of 300 nm. All measurements were conducted at a temperature of 64° C.

Figure 7:
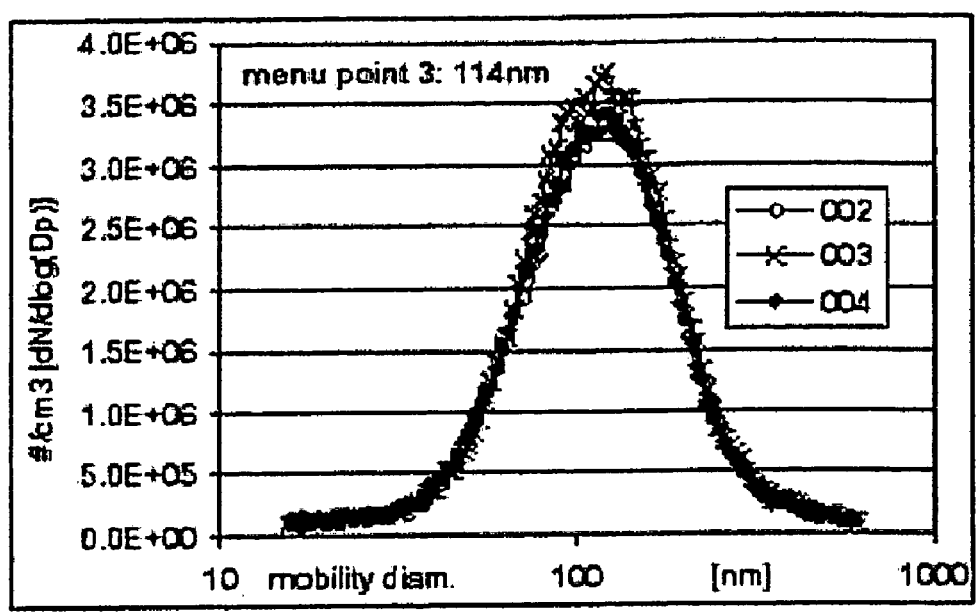
FIG. 7 is a diagram of a typical particle distribution by size.

Using the Filter Smoke Number (or the paper blackening), on the one hand, and the particle concentration of soot particles in mg/m$^3$ (=filter loading/suction length in m) resulting from this and, on the other hand, the mean particle diameter, it is furthermore possible—assuming a typical particle distribution, normally a log normal distribution—to indicate an approximation value for the particle number as well. FIG. 7, for example, shows a typical particle size distribution for particles of a mean diameter of approximately 110 nm. Based on the measured total mass on the filter, the mean diameter and the assumption of a typical log normal distribution, it is possible to calculate a total particle number.

Since the correlation between particle diameter, particle type and mean particle size with the differential pressure on the filter paper and/or the change of this differential pressure during measurements on the filter paper also applies for gravimetric measurements, it is possible using similar and/or equivalent methods—the measurement of the mass of insoluble and soluble components of particles deposited on a filter—and the measurement of the differential pressure on the filter at different points in time of the specific filter loading or the measurement of the change of the differential pressure/(time unit and mass loading unit) during the filter loading to extrapolate the information relative to the mean particle diameter as well.

In principle, this methodology for the determination of the particle size is generally applicable and not only for soot particles, provided simultaneously with the determination of the mass (gravimetrically, by weighing or by means of other methods such as e.g. infrared absorption or opacimetry . . . supplying values which are proportional to the mass or the concentration) the change of the differential pressure during the loading of the filter or of the filters is also determined as a parameter of measurement.

Regarding more complex particle compositions (bimodal particle distributions, with/without HC, with/without sulfates . . . ), it is possible for the additional selection of the parameters to conduct simultaneous, parallel measurements via two or even several filters and to determine the particle diameters and particle type by means of the time-specific functions of the measured parameters. If the particle type and/or composition does not change during the measurement, naturally, it is also possible to conduct the measurements in sequence.

Finally, it is to be noted that, aside from the conventional filters and filter papers for the method according to the invention, it is also possible to employ membrane filters and sintering filters made of polymers and metallic materials.

The fiber filters made of cotton or glass fiber have an inherently minimal pressure drop even with larger gas flows, meaning they are able to collect large amounts of material of the most varied particle size distributions/diameters very quickly on the fiber surfaces.

Glass fiber filters with/without polymer coating can be thermostatitized—if necessary—up to 190° C. and are chemically inert. The addressed cotton filters are standardized for the "measuring of soot" in accordance with the filtering method.

Using different filters with differing particle collection characteristics also allows for modifying and/or adjusting the efficiency of the collection for certain particle sizes or particle types. This way, it is possible or it would be possible to satisfy special requirements during the measuring process by way of the paper that is used, either for very small or very large particle sizes or also certain particle types (hydrocarbons, tars, sulfates, aerosols, . . . dust, more or less intermixed with soot).

I claim:

1. Method for determining characteristic properties of soot particles originating from combustion processes, comprising the steps of moving the soot particles towards a filter paper, depositing the soot particles on the filter paper, determining a degree of blackening of said filter paper due to retention of the soot particles thereon, determining a differential pressure on the filter paper due to deposition of the soot particles thereon at predetermined intervals, and determining at least one of particle mass, particle diameter, type of particle and particle distribution of the soot particles from a predetermined functional correlation of the paper blackening with the differential pressure.

2. Method as claimed in claim 1, wherein a face velocity of the filter surface is in the range of 1 to 200 cm/sec.

3. Method as claimed in claim 2, wherein the face velocity is 5 to 50 cm/sec.

4. Method as claimed in claim 1, comprising the step of determining an absolute pressure upstream and downstream of the filter.

5. Method as claimed in claim 1, comprising the step of determining pressure in relation to the ambient air pressure upstream and downstream of the filter.

6. Method as claimed in claim 1, comprising the step of determining differential pressure across the filter and the absolute pressure of the ambient air.

7. Method as claimed in claim 1, comprising the step of determining temperature close to a surface of the filter.

8. Method as claimed in claim 7, wherein the filter is maintained at a constant temperature in the range of 50 to 190° C.

9. Method as claimed in claim 8, wherein the temperature is between 60 and 70° C.

10. Method as claimed in claim 8, wherein a temperature of a particle-laden measuring gas is regulated to the same temperature as the filter and/or an inside temperature of the measuring device.

11. Method as claimed in claim 10, wherein changes of suction length are determined relative to the suction length determined during measurements on clean papers in ultrapure air, and corresponding values are always related to the same general conditions.

12. Method as claimed in claim 11, wherein the measurement takes place with at least one preset differential pressure value on the filter paper.

13. Method as claimed in claim 12, wherein the preset differential pressure threshold values are in the range of 0 to 300 mbar.

14. Method as claimed in claim 13, wherein the preset differential pressure threshold values range between 25 and 200 mbar.

15. Method as claimed in claim 11, wherein measurement takes place with at least one preset negative pressure value after the filter.

16. Method as claimed in claim 15, wherein these preset negative pressure threshold values are in the range of 50 to 450 mbar.

17. Method as claimed in claim 16, wherein the preset negative pressure threshold values range between 50 and 300 mbar.

18. Method as claimed in claim 17, wherein the measurements are taken at least with two different suction lengths.

19. Method as claimed in claim 18, wherein the measurements are taken at least with two different differential pressures and/negative pressures.

20. Method as claimed in claim 19, wherein the change of the differential pressure on the filter paper and/or of the negative pressure downstream of the filter paper is/are determined along with the duration of the specific filter loading and the value of the specific filter loading established at the end of the loading of the filter.

21. Method as claimed in claim 1, including a measuring device and wherein filter temperature and/or an inside temperature of the measuring device are kept constant.

22. Method for determining characteristic properties of soot particles originating from combustion processes, comprising the steps of depositing the soot particles on a filter paper, determining a degree of blackening of said filter paper due to retention of the soot particles thereon, determining a differential pressure on the filter paper due to deposition of the soot particles thereon measured integrally, and determining at least one of particle mass, particle diameter, type of particle and particle distribution of the soot particles from a predetermined functional correlation of the paper blackening with the differential pressure.

* * * * *